United States Patent [19]

Stache et al.

[11] 3,937,697

[45] Feb. 10, 1976

[54] 12-DEHYDRO DIGOXIN-4'''-AND 3'''-ALKYL ETHERS

[75] Inventors: Ulrich Stache, Hofheim, Taunus; Werner Fritsch, Neuenhain, Taunus; Werner Haede, Hofheim, Taunus; Ernest Lindner, Frankfurt am Main, all of Germany

[73] Assignee: Hoechst Aktiengesellschaft, Frankfurt am Main, Germany

[22] Filed: Feb. 28, 1975

[21] Appl. No.: 554,182

[30] Foreign Application Priority Data

Mar. 2, 1974 Germany............................ 2410012

[52] U.S. Cl............................. 260/210.5; 424/182
[51] Int. Cl.²........................................ C07J 19/00
[58] Field of Search................................ 260/210.5

[56] References Cited

FOREIGN PATENTS OR APPLICATIONS 1,961,034  12/1971  Germany.......................... 260/210.5

OTHER PUBLICATIONS

Wagner and Zook, Syn. Org. Chem., Wiley and Sons Inc., 1953, p. 323.

Primary Examiner—Lewis Gotts
Assistant Examiner—Cary Owens
Attorney, Agent, or Firm—Curtis, Morris & Safford

[57] ABSTRACT

12-Dehydro digoxin mono-4''' and 3'''-alkyl ethers and a process for their manufacture.

The compounds have a cardiotonic and diuretic activity.

4 Claims, No Drawings

12-DEHYDRO DIGOXIN-4'''-AND 3'''-ALKYL ETHERS

The present invention relates to 12-dehydro digoxin-mono-4'''- and 3'''-alkyl ethers of the formula I

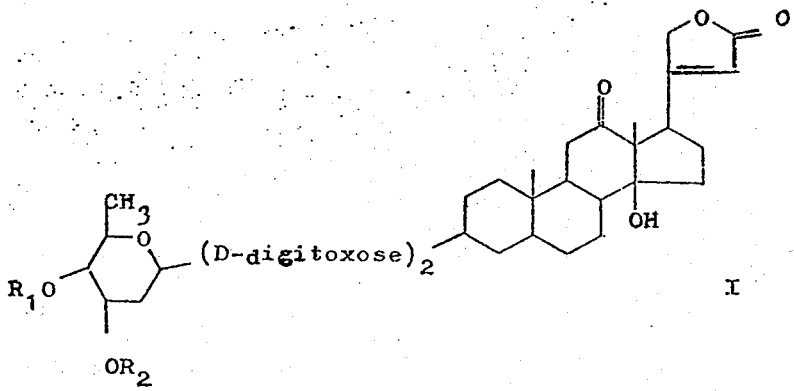

in which $R_1$ and $R_2$ are different and each stands for a hydrogen atom or a lower alkyl group of 1 to 4 carbon atoms.

This invention further relates to a process for the manufacture of 12-dehydro digoxin mono-4'''- or 3'''-alkyl ethers of formula I, which comprises (a) oxidizing a digoxin mono-4'''- or 3'''-alkyl ether of the formula II

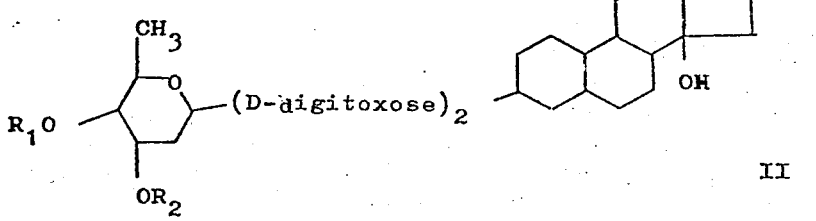

in which $R_1$ and $R_2$ are defined as above, with an oxidizing agent to yield the compounds of formula I, or b. reacting 12-dehydro digoxin in an analogous manner with a dialkyl sulfate of the formula III

$(R_3O)_2SO_2$   III in which $R_3$ stands for a lower alkyl group of 1 to 4 carbon atoms, in dimethylformamide in the presence of barium hydroxide while adding either aluminium oxide to yield the compounds of formula I, wherein $R_1$ stands for alkyl of 1 to 4 carbon atoms and $R_2$ for hydrogen, or while adding aluminium isopropylate to yield compounds of formula I, wherein $R_1$ is hydrogen and $R_2$ alkyl of 1 to 4 carbon atoms.

According to method (a) of this process, the 12-β-hydroxy group in the aglucone moiety is selectively oxidized to yield the 12-oxo group, without affecting the hydroxy groups also present in this glucose moiety in 3'-, 3''- and 3''' or 4'''-positions. The oxidation reaction is carried out by the usual methods, preferably methods using chromium trioxide as oxidizing agent, such as the oxidation methods according to Jones, Kiliani or Sarrett.

According to a particularly advantageous embodiment of this process, the compounds of formula II are dissolved in a mixture of solvents, such as acetone/dioxan/water, and treated with a solution of chrominum trioxide in water/sulfuric acid at temperatures of from —30° to +100°C, preferably from —10° to +50°C. The mixture is then worked up by pouring it into water, extracting it with a solvent, preferably chloroform or methylene chloride, washing the extracts with water and removing the solvents by distillation. The foamy residue obtained may be crystallized either directly or upon chromatography from inert organic solvents. The crystallized reaction products thus obtained may moveover, where required, be recrystallized from inert organic solvents. The starting compounds of formula II used for this reaction may be obtained, for example according to the process disclosed in German Offenlegungsschrift No. 1,961,034, by reacting digoxin with a dialkyl sulfate in the presence of barium hydroxide while adding aluminium oxide or aluminium propylate.

According to method (b) of this process, exclusively the 4'''- or 3'''-hydroxy group in the terminal digitoxose of 12-dehydro-digoxin is selectively alkylated according to known methods, depending on which substitution product is to be obtained. To prepare the 4'''-monoalkyl ethers of 12-dehydro digoxin, especially the 4'''-methyl ether, 12-dehydro digoxin is reacted according to the process of the above-cited German Offenlegungsschrift with dialkyl sulfates, for example dimethyl, diethyl, dipropyl or dibutyl sulfate, especially with dimethyl sulfate, in the presence of barium hydroxide in an inert solvent, such as benzene, toluene, cyclohexane or a chlorinated hydrocarbon, while adding aluminium oxide. To prepare 3'''-monoalkyl ethers of 12-dehydro digoxin, especially the 3'''-methyl ether, the reaction is analogous, except for using, instead of aluminium oxide, the aluminium iso-propylate which brings about a special alkylation of the 3'''-hydroxy group instead of the 4'''-group as caused by using aluminium oxide.

The 12-dehydro digoxin serving as a starting product for method (b) is prepared in a manner analogous to method (a) by selective oxidation of digoxin in the 12-position.

To work up and obtain the products of the invention in pure state from the reaction mixtures obtained, the crude products obtained upon concentration are separated, mainly from unreacted 12-dehydro digoxin used, by chromatography using silica gel or aluminium oxide. The crude product may also be separated into its homogenous components by the usual multiplicative distribution. After this, the products thus obtained may be recrystallized from adequate inert organic solvents.

The products obtained according to the invention have valuable pharmacological properties, for example cardiotonic and diuretic effects. Especially striking is their high positively inotropic activity established on the isolated heart of a guinea pig in an atrium test or by potassium secretion. Surprisingly, this inotropic effect appears in a significant manner already at a dose which is far below the normal dose, at which first toxic symptoms, such as a disturbed cardiac rythm or disturbances of the atrioventricular conduction and conduction along the Purkenje system, are observed. Their toxicity as tested on rats and mice is very low.

Compared with the 4'''- or 3'''-alkyl digoxin derivatives, from which they are derived, the products of the invention show an improved therapeutic index, especially demonstrable on the twin preparation 4'''-O-methyl-12-dehydro digoxin/4'''—O—methyl digoxin (i.e. β-methyl digoxin).

Moreover, the new compounds exhibit a complete enteral absorption, thus allowing optimum control, especially in the oral administration of the products of the invention. Therefore these products may be used for the treatment of heart diseases, in particular of cardiac insufficiency and tachycardia, especially in those cases where digoxin and its derivatives β-methyl-digoxin or α- and β-acetyl digoxin already cause cardiotoxic side effects when administered at an adequately high dosage. The individual dosage unit to be administered to humans ranges from about 0.05 to 1 mg, the daily dosage from about 3 to 4 times that of the individual dosage.

The administration is preferably by the oral route in the form of tablets, capsules, dragees which may contain the usual pharmaceutical carriers, for example starch, lactose, tragacanth, magnesium stearate and talcum.

For use in intravenous injections, water or a physiological sodium chloride solution may be considered.

The following Examples illustrate the invention.

EXAMPLE 1

4'''—O—Methyl-12-dehydro digoxin

A solution of 200 mg of chromium trioxide in 20 ml of acetic acid was added dropwise within 30 minutes to a solution of 2.15 g of 4'''-O-methyl digoxin in 80 ml of glacial acetic acid. After stirring for 3 hours at 20°C, further oxidizing agent (400 mg of CrO₃ in 40 ml of glacial acetic acid and 1 ml of water) was added dropwise for 3 hours. When there was still starting material to be established in the thin-layer chromatogram, another 20 ml of the above oxidizing agent were added, and stirring was continued at 20°C until the reaction was complete (according to the thin-layer chromatogram).

For the work-up, the reaction mixture was poured into 1 l of water, extracted several times with methylene chloride, washed with water, dried with sodium sulfate, and the solvents were eliminated by distillation in vacuo. 1.8 Grams of a crude product were obtained, which was chromatographed on silica gel "Merck" (size of column: height: 22 cm, diameter: 3 cm) using a 99:1 mixture of methylene chloride and methanol as eluent, to yield the pure product. The passage of 1 l of eluent yielded 210 mg of a mixture consisting predominantly of the product of the invention and a compound which was unpolar in the thin-layer chromatogram, the passage of another 4 l of eluent yielded, upon distillation, 1.3 g of chromatographically homogenous foam which, upon crystallization from acetone/ether, gave a yield of 1.1 g of 4'''-O-methyl-12-dehydro digoxin; melting point: 205°C (determined in a Tottoli apparatus).

EXAMPLE 2

4'''—O—Ethyl-12-dehydro digoxin

In the same manner as disclosed in Example 1, a solution of 2.15 g of 4'''-O-ethyl digoxin in 80 ml of glacial acetic acid was oxidized with chromium trioxide in acetic acid. Upon corresponding work-up and chromatography on silica gel, recrystallisation from acetone/ether yielded 1.1 g of 4'''—O—ethyl-12-dehydro digoxin having a melting point of 160°–165°C.

EXAMPLE 3

3'''—O—Methyl-12-dehydro digoxin

In the same manner as disclosed in Example 1, a solution of 2.15 g of 3'''-O-methyl digoxin in 80 ml of glacial acetic acid was oxidized with chromium trioxide in acetic acid. Upon an analogous work-up and chromatography on silica gel, recrystallization from acetone ether yielded 1.1 g of 3'''—O—methyl-12-dehydro digoxin, having a melting point of 232°–235°C.

EXAMPLE 4

4'''-O-methyl-12-dehydro digoxin 7.5 Milliliters of a Jones-type reactant solution (26.67 g of CrO₃ combined with 23 ml of concentrated sulfuric acid and diluted with water to a volume of 100 ml) were added dropwise for about 10 minutes to a solution of 1 g of 4'''—O—methyl digoxin in 85 ml of acetone, while maintaining a temperature of at most 30°C. After stirring for 15 minutes at 20°C, undissolved material was separated by decanting, and the reaction mixture was poured into water. After extraction with methylene chloride, washing with water, drying with sodium sulfate, the organic solvent was distilled off in vacuo. The residue obtained was chromatographed as disclosed in Example 1 using silica gel, and upon recrystallization from acetone/ether the same reaction product having the same characteristic data as in Example 1 was obtained.

EXAMPLE 5

12-Dehydro digoxin

In the same manner as disclosed in Example 1, a solution of 2.15 g of digoxin in 80 ml of glacial acetic acid was oxidized with chromium trioxide in acetic acid. Upon an analogous work-up as in Example 1, recrystallization from acetone/ether yielded 1.5 g of 12-dehydro digoxin having a melting point of 275°–278°C.

EXAMPLE 6

4'''-O-Methyl-12-dehydro digoxin

A solution of 2.4 ml of dimethyl sulfate in 24 ml of absolute toluene was added dropwise at 20°C for 1 hour, upon addition of 1.8 g of barium hydroxide and 2.4 g of aluminium oxide; to a solution of 3 g of 12-dehydro digoxin in 24 ml of absolute dimethylformamide and 24 ml of absolute toluene. After stirring for 24 hours at 20°C, the reaction mixture was diluted with 100 ml of chloroform. The mixture was filtered through a clarifying-layer filter covered with silica gel, washed with 250 ml of chloroform and 15 ml of pyridine. Upon concentration in vacuo, the residue was taken up with 300 ml of cloroform, washed twice with water and dried. The washing waters were also shaken with chloroform. The combined organic extracts were then concentrated in vacuo, and the residue obtained was chromatographed on silica gel Merck (column size: height: 17 cm, diameter: 4.5 cm). Upon elution of 2 l of methylene chloride and 3 l of methylene chloride/methanol (99:1) (these eluates did not contain the desired 4'''-monomethyl ether), the product was eluted with 6 l of a 98:2 mixture of methylene chloride and methanol. Upon distillation of the solvent of the last eluate, recrystallization yielded the 4'''-O-methyl-12-dehydro digoxin having the same characteristic data as the product obtained according to Example 1.

We claim:

1. A compound of the formula I

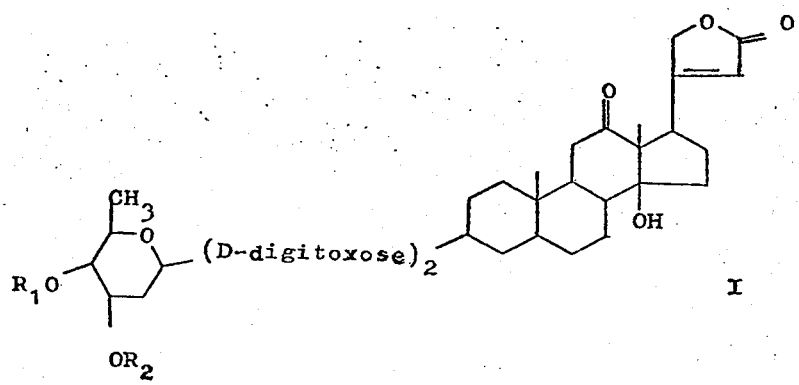

in which $R_1$ and $R_2$ are different and each stands for hydrogen or lower alkyl of 1 to 4 carbon atoms.

2. A compound as claimed in claim 1 which is 4''λ'—O—-methyl-12-dehydro digoxin.

3. A compound as claimed in claim 1 which is 4'''-O-ethyl-12-dehydro digoxin.

4. A compound as claimed in claim 1 which is 3'''-O-methyl-12-dehydro digoxin.

* * * * *